US012263335B2

(12) United States Patent
Oakley et al.

(10) Patent No.: US 12,263,335 B2
(45) Date of Patent: Apr. 1, 2025

(54) COOLING OF A DRIVE SYSTEM FOR DIAPHRAGM PUMPS

(71) Applicant: Berlin Heart GmbH, Berlin (DE)

(72) Inventors: Matthew Oakley, Warendorf (DE); Norbert Schwiertz, Strausberg (DE)

(73) Assignee: Berlin Heart GmbH, Berlin (DE)

( * ) Notice: Subject to any disclaimer, the term of this patent is extended or adjusted under 35 U.S.C. 154(b) by 412 days.

(21) Appl. No.: 17/423,099

(22) PCT Filed: Jan. 15, 2020

(86) PCT No.: PCT/EP2020/050925
§ 371 (c)(1),
(2) Date: Jul. 14, 2021

(87) PCT Pub. No.: WO2020/148341
PCT Pub. Date: Jul. 23, 2020

(65) Prior Publication Data
US 2022/0126084 A1   Apr. 28, 2022

(30) Foreign Application Priority Data

Jan. 15, 2019  (EP) ..................... 19151949

(51) Int. Cl.
*F04B 43/04*   (2006.01)
*A61M 60/104*   (2021.01)
(Continued)

(52) U.S. Cl.
CPC ........ *A61M 60/441* (2021.01); *A61M 60/104* (2021.01); *A61M 60/117* (2021.01);
(Continued)

(58) Field of Classification Search
CPC .... F04B 5/00; F04B 5/02; F04B 43/02; F04B 43/025; F04B 43/06; F04B 43/067;
(Continued)

(56) References Cited

U.S. PATENT DOCUMENTS 3,168,047 A * 2/1965 Hardman .................. F04B 7/00
417/415
3,674,381 A   7/1972 Schiff
(Continued)

FOREIGN PATENT DOCUMENTS

WO   WO 2016034286 A1   3/2016

OTHER PUBLICATIONS

International Search Report, issued in International Patent Application No. PCT/EP2020/050925, dated Mar. 27, 2020, pp. 1-10, European Patent Office, Rijswijk, Netherlands.

*Primary Examiner* — Philip E Stimpert
(74) *Attorney, Agent, or Firm* — Crowell & Moring LLP

(57) ABSTRACT

A drive unit for a diaphragm pump may be provided, wherein the drive unit comprises a hollow body and a piston which is arranged so as to be movable in the first hollow body along an axis of the hollow body, wherein the piston divides the hollow body into a first chamber, which is connectable to the diaphragm pump, and a second chamber, which is coupleable to a gas reservoir. The second chamber comprises an inlet valve and an outlet valve, such that a gas flow is drawn into the chamber via the inlet valve and is forced out of the chamber via the outlet valve.

8 Claims, 4 Drawing Sheets

(51) Int. Cl.
*A61M 60/117* (2021.01)
*A61M 60/258* (2021.01)
*A61M 60/268* (2021.01)
*A61M 60/435* (2021.01)
*A61M 60/441* (2021.01)
*A61M 60/835* (2021.01)
*F04B 5/00* (2006.01)
*F04B 23/06* (2006.01)

(52) U.S. Cl.
CPC ........ *A61M 60/258* (2021.01); *A61M 60/268* (2021.01); *A61M 60/435* (2021.01); *A61M 60/835* (2021.01); *F04B 5/00* (2013.01); *F04B 23/06* (2013.01); *F04B 43/04* (2013.01)

(58) Field of Classification Search
CPC ........ F04B 43/073; F04B 53/08; F04B 39/06; F04B 23/06; F04D 29/5806; F04D 29/5813
USPC .............................. 417/392, 395, 383, 199.1
See application file for complete search history.

(56) References Cited

U.S. PATENT DOCUMENTS

| | | | | |
|---|---|---|---|---|
| 3,736,074 | A | * | 5/1973 | Kilbane .............. F04B 39/0033 415/58.4 |
| 3,966,358 | A | | 6/1976 | Heimes et al. |
| 2002/0071779 | A1 | * | 6/2002 | Moroi .................. F04C 23/008 418/83 |
| 2007/0116588 | A1 | * | 5/2007 | Frefel ...................... F04B 5/02 417/521 |
| 2012/0192710 | A1 | * | 8/2012 | Moore .................. F04B 39/121 92/12.2 |
| 2015/0354553 | A1 | * | 12/2015 | Nagura .................. F04B 39/06 417/243 |

* cited by examiner

COOLING OF A DRIVE SYSTEM FOR DIAPHRAGM PUMPS

CROSS-REFERENCE TO RELATED APPLICATIONS

This application is a 371 nationalization of international patent application PCT/EP2020/050925 filed Jan. 15, 2020, which claims priority under 35 USC § 119 to European patent application 19151949.5 filed Jan. 15, 2019. The entire contents of each of the above-identified applications are hereby incorporated by reference.

BRIEF DESCRIPTIONS OF DRAWINGS

Figure 1:
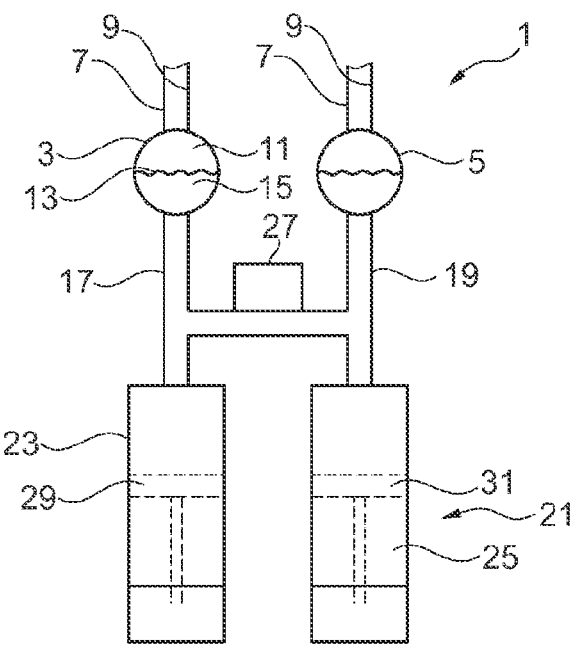
Figure 2:
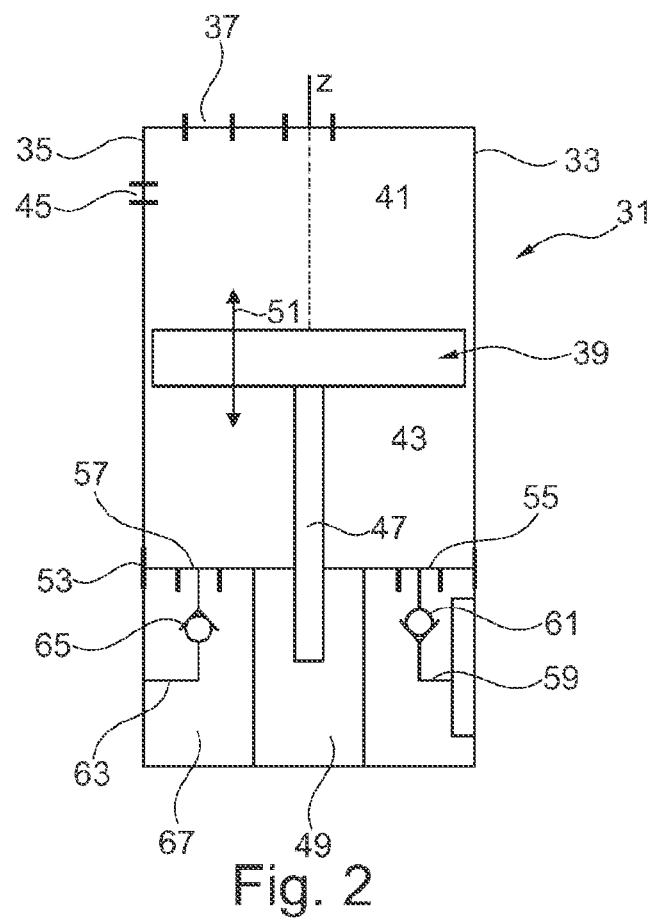
Figure 3:
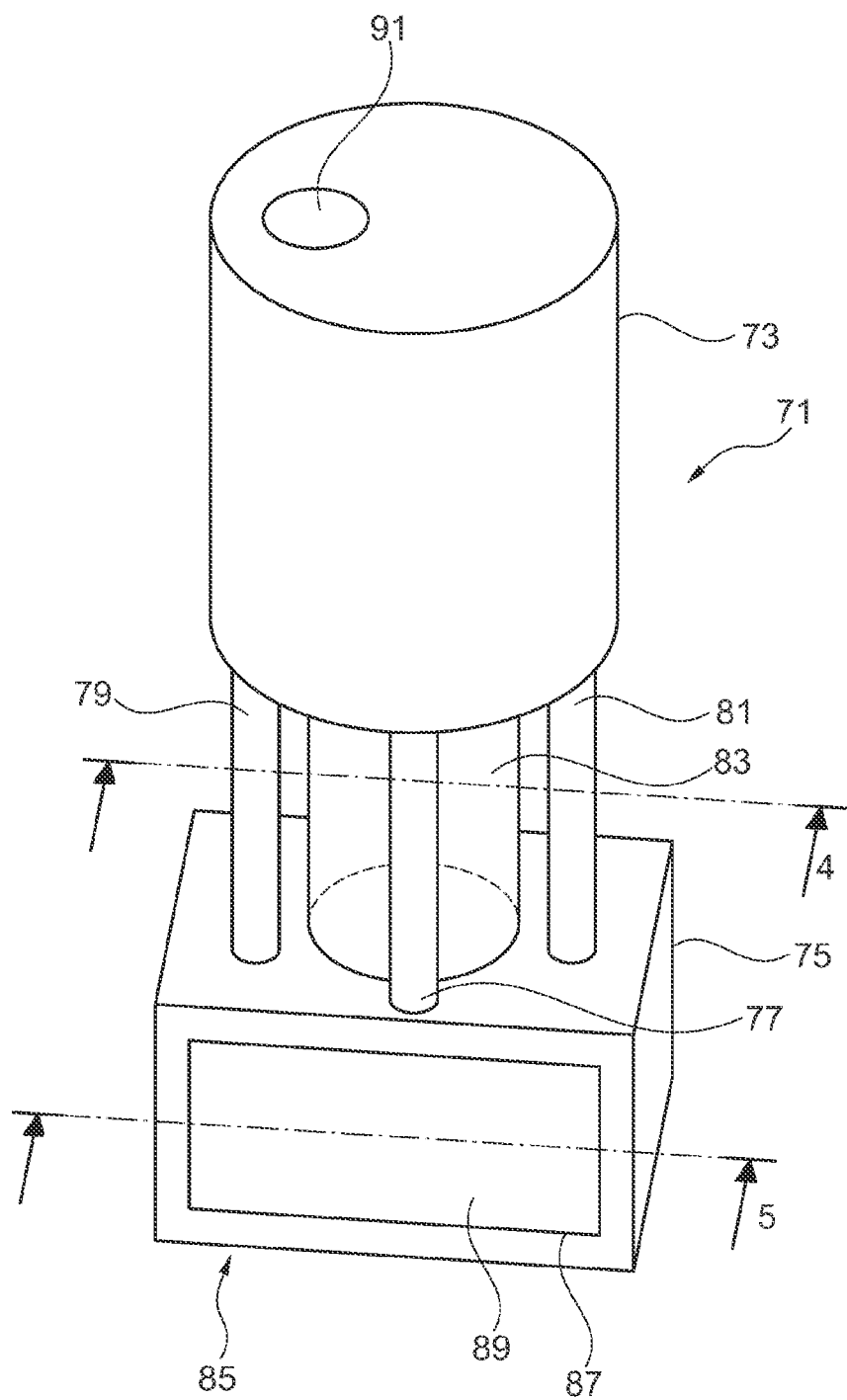
Figure 4:
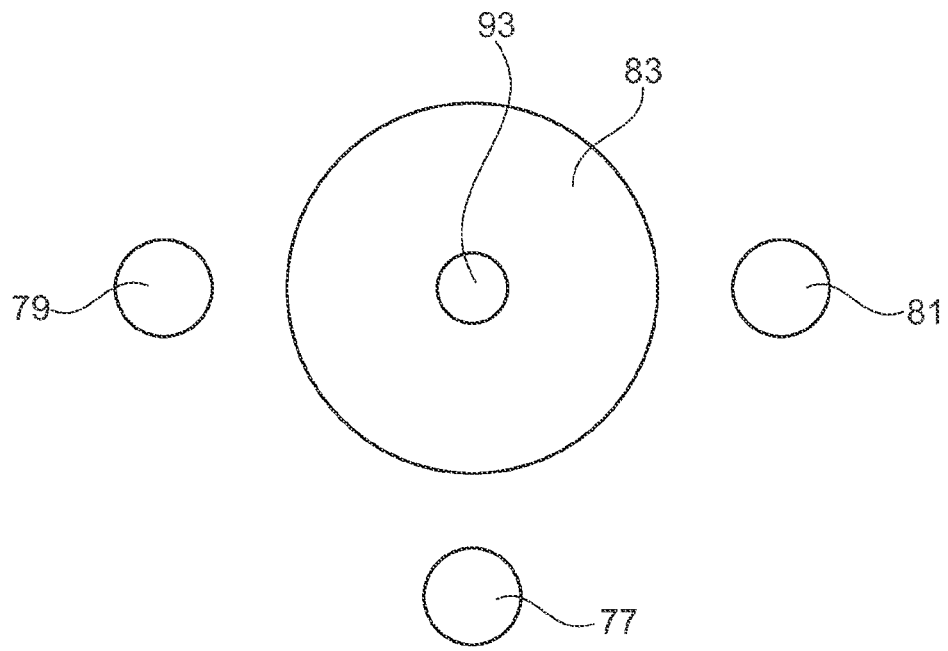
Figure 5:
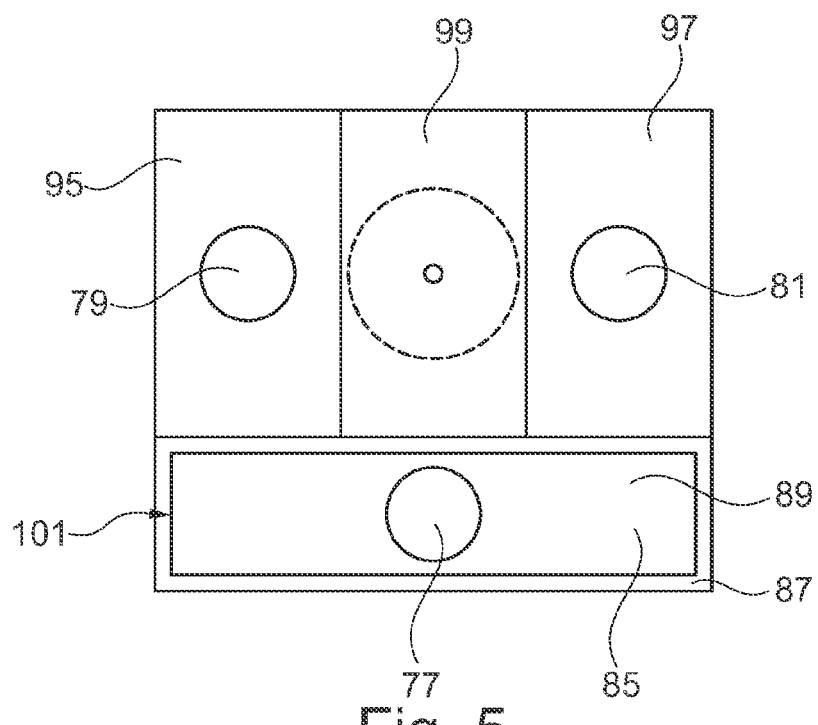
Figure 6:
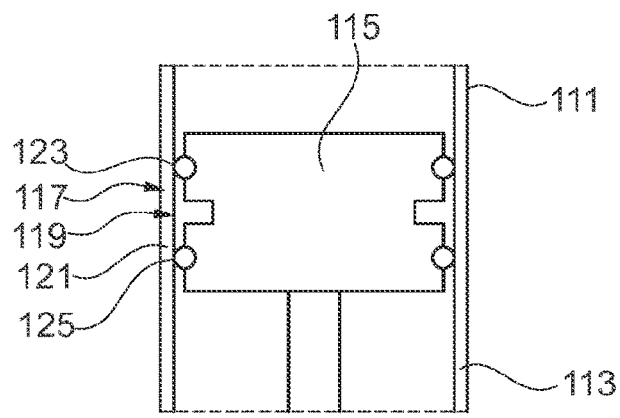

FIG. 1 shows a schematic view of a VAD system with two diaphragm pumps and a drive system with a control unit and two drive units;
FIG. 2 shows a schematic longitudinal section through a drive unit;
FIG. 3 shows a spatial representation of a drive unit;
FIG. 4 shows a cross-section through the drive unit of FIG. 3;
FIG. 5 shows a further cross-section through the drive unit of FIG. 3;
FIG. 6 shows a longitudinal section through the drive unit of FIG. 3; and
FIGS. 7(a) to (d) show a schematic illustration of an intake and discharge operation by means of a drive unit described herein.

DETAILED DESCRIPTION

The present invention relates to a drive unit, in particular for a diaphragm pump. Diaphragm pumps are used in extracorporeal cardiac support systems, so-called Ventricular Assist Devices (VADs). In order to be able to control the diaphragm pumps very precisely, numerous factors must interact. Among other things, it is important that the drive unit controls the diaphragm pump precisely in terms of timing and volume so that the blood in the diaphragm pump can be pumped into or drawn out of the bloodstream.

The reliability of the drive unit is of high importance in order to guarantee the patient a sufficient blood supply. The drive system should be able to dissipate the heat generated by friction or pressure. It has been shown that in particular the maintenance to be carried out increases if the heat cannot be reliably removed from the drive unit of the drive system. Uneven distribution of heat within the drive system in a drive unit leads to local hotspots, which cause leaks, for example, which in turn result in a more uneven supply of compressed air to the diaphragm pump.

The drive unit for a diaphragm pump comprises a first hollow body and a piston arranged in the first hollow body to be movable along an axis of the hollow body. The piston divides the hollow body into a first chamber connected to the diaphragm pump and a second chamber which can be coupled to a gas reservoir. The hollow body can be, for example, a cylinder in which a round piston runs. The air (or another gas or fluid) present in the first chamber can lift or relax the diaphragm of the diaphragm pump and thereby create a negative or positive pressure in the second chamber of the diaphragm pump so that blood can be expelled or drawn in.

Due to the compression of the gas or air in the first chamber, the hollow body is heated. This heat can be removed from the drive unit via the hollow body itself on the one hand and, on the other hand, via the gas contained in the second chamber of the drive unit.

The second chamber is connected to the surroundings via an inlet valve and an outlet valve. A gas flow, usually ambient air, is drawn into the chamber from the external environment by means of the inlet valve and forced out of the chamber via the outlet valve. By means of the inlet and outlet valves it is possible to create a directed air flow in the second chamber of the drive unit. This ensures that only air from outside the drive unit is drawn into the second chamber through the inlet valve and that this air is preferably completely discharged to the outside environment via the outlet valve. In numerous embodiments, the inlet valve and the outlet valve are designed to be separate from each other. This ensures that the air, which is often colder than the air in the second chamber when it is drawn in from the outside, warms up in the second chamber and warmed air is completely expelled via the outlet valve. By means of the inlet and outlet valves it is therefore possible to create a directed air flow through the second chamber. In this way, the temperature inside the drive unit can be kept lower and evenly distributed, i.e. without local hotspots.

In one embodiment, an inlet and an outlet are provided in the chamber, i.e. the inlet and the outlet are separated from each other. The inlet is then coupled to the inlet valve and the outlet is coupled to the outlet valve. In other words, the supply line connecting the inlet to the inlet valve is different from the supply line connecting the outlet to the outlet valve. By separating the inlet and outlet, the direction of the airflow through the chamber is assisted.

The inlet valve and/or the outlet valve can preferably be designed as a check valve. For example, check valves may be of simple design, such as mechanical check valves. The check valves allow for directional airflow and do not require any electronic circuitry. Furthermore, the check valves may also be selected so that the force for opening the valves is matched to the operating parameters of the drive unit. For example, the check valves may be spring-loaded or electronically actuated check valves. In other variations, one of the valves may be a shut-off valve that is electronically regulated.

Additionally or optionally, the drive unit may comprise a filter unit, wherein the inlet valve preferably fluidically couples the filter unit and the second chamber with each other. The filter unit ensures that dirt and suspended particles cannot enter the second chamber. This extends the maintenance cycles for the drive unit. In the filter unit, for example, a textile filter, a ceramic filter or other filters known in the prior art may be used for air filtration.

Alternatively or additionally, the filter unit is a replaceable filter, the filter preferably being held between a filter bowl and a filter cover. A replaceable filter unit has the advantage that the filter unit can be replaced in regular maintenance cycles, thus avoiding clogging of the filter.

Alternatively or additionally, the drive unit may be configured such that connecting elements connecting the inlet or outlet valve, respectively, to the second chamber have a different cross-section from each other. For example, the tube connected to the inlet valve may have a smaller cross-sectional area than the tube connected to the outlet valve. As a result, the sucked-in air flow is drawn in at a higher speed, so that the second chamber has strong turbulence and the sucked-in air is distributed evenly over the first chamber. Because the cross-sectional area of the connecting element connected to the outlet valve is larger, the air or the gas sucked in is not additionally heated when it is expelled, but is merely pressed gently through the outlet or the outlet valve.

Alternatively or additionally, the drive unit further comprises at least one heat sink, wherein the outlet valve fluidically couples the heat sink to the second chamber. The heat sinks are arranged in such a way that they are located in the immediate vicinity of a motor which moves the piston arranged in the hollow body. The waste heat generated by the motor is then immediately dissipated to the environment via the heat sinks. Here, it is advantageous if the motor is thermally coupled to the at least one heat sink.

In addition to the directed air flow, the heat input into the drive unit can also be reduced if there is a gap seal between the inner wall of the hollow body and the piston. This gap seal forms a barrier built up between the first and second chambers. For example, the gap seal may comprise at least one O-ring, preferably guided in at least one groove of the piston. The O-ring may be a O-ring made from Viton, for example.

Another measure to regulate heat is to cover the inside of the hollow body with a thermal coating. Thermal coatings that can be used here include diamondlike carbon (DLC) or PTFE coatings.

Alternatively or additionally, the outer wall of the hollow body may have cooling fins which are also intended to better dissipate the heat introduced into the hollow body to the outside.

Further embodiments are explained in the following embodiments. The aforementioned features may each be implemented individually and separately in the embodiments, even if the embodiments themselves comprise several of the individual features.

FIG. 1 schematically shows an extracorporeal VAD system with drive unit, such as is commercially available from Berlin Heart as ®EXCOR with the IKUS drive unit. The VAD system 1 comprises a first diaphragm pump 3 and a second diaphragm pump 5, which are connected to a chamber of the heart, for example the left ventricle, by means of lines 7 and 9. In this case, the pump is configured such that, for example, blood is drawn into the first chamber 11 of the diaphragm pump through the tubing line and is expelled from the chamber 11 into the heart through the second line 9.

Inside the diaphragm pump, a diaphragm 13 is arranged to separate the first chamber 11, which can be filled with blood, from the air chamber 15. The air chamber 15 is connected to the drive system via another line 17. The drive system 21 comprises a first drive unit 23 and a second drive unit 25, each connected to one of the diaphragm pumps 3 and 5 via one of the air lines 17 and 19. The drive units 23 and 25 are controlled by means of a control unit 27, so that the piston 29 or 31 arranged in the drive units 23 and 25 fills the chamber 15 or the corresponding chamber of the diaphragm pump 5 with gas or extracts the gas, respectively.

The drive unit 23 will be explained in more detail with reference to FIG. 2. The drive unit 31 shown in FIG. 2 comprises a hollow body 33, which in the present example is designed as a cylinder with a cylinder axis z. The cylinder is sealed airtight at its upper end by means of a cover 35 and has an opening 37 which can be connected to an air or gas line, such as line 17 or 19. As an alternative to a pure opening, there may also be a port for direct connection of the line.

A piston 39 is disposed within the hollow body 33, dividing the interior of the hollow body 33 into a first chamber 41 and a second chamber 43. The first chamber 41 is adapted to be fluidically connected to the diaphragm pumps or one of the diaphragm pumps. The second chamber 43 is configured to be filled with gas or air and to expel said gas or air, respectively. For example, if for some reason there is leakage in the first chamber 41, it can draw in additional air by means of another port 45. The port can be connected to a filter unit, for example.

The piston 39 is connected to a spindle 47 which is rotated by means of a drive unit 49 in the form of an electric motor. This can produce a piston stroke 51 such that the volume of the first chamber 41 is reduced and the volume of the second chamber 43 is correspondingly increased, or vice versa.

The lower chamber 43 is closed off by means of a lower cover 53. The spindle 47 is guided by means of seals through the cover 53, which is designed as a plate. Further, the plate includes an inlet 55 and an outlet 57 separate from the inlet. The inlet is connected to the surroundings via a line 59. An inlet valve 61 is disposed in this line, which in the present example is configured as a check valve such that air cannot escape through the inlet 55 to the surroundings. Similarly, the outlet 57 is connected to the surroundings by means of a line 63, the line 63 having an outlet valve 65 which allows air to escape in the outlet direction and blocks it in the intake direction. The outlet line 63 is located within a heat sink 67, which is thermally coupled to the motor 49 by applying a thermal compound to the motor that is bonded to the heat sink.

FIG. 3 again shows a spatial representation of a drive unit. The drive unit 71 comprises a cylindrical hollow body 73 and a drive unit arranged below the hollow body 73 within the suction or discharge block 75, which is coupled to the hollow body 73 by means of the inlet line 77 and the outlet lines 79 and 81. An inlet valve is arranged in the inlet line 77, and an outlet valve is arranged in each of the outlet lines 79 and 81. A spindle, not shown in FIG. 3, passes through block 83 coupling the motor to the piston.

In addition to a motor not shown in this embodiment, the intake block 75 includes a filter unit 85 comprising a filter frame 87, a textile replaceable filter 89 located therebehind, and a filter bowl 101 filled by the replaceable filter 89. At the upper end of the hollow body 73 is a port 91 through which a chamber of the hollow body can be connected to a diaphragm pump. The hollow body shown herein is made of a metal and, in another embodiment, may include cooling fins extending around the outside of the hollow body. The drive block 75 may also be formed from multiple components and may be made of metal, such as machined aluminum or titanium.

FIG. 4 shows a cross-section through the outlet lines 79 and 81, the inlet lines 77 and the block 83 in which the spindle 93 runs. It can be clearly seen that the cross-section of the inlet 77 is smaller than the cross-section of the combined outlets 79 and 81. In this way, the air or gas flow is accelerated during suction and guided into the chamber, thus ensuring additional mixing of the air present in the second chamber of the hollow body. When the air is subsequently expelled, a larger cross-section is available, so that the air is only heated to a small extent.

FIG. 5 shows a further cross-section through the drive unit of FIG. 3. Again, outlet lines 79 and 81 can be seen extending through heat sinks 95 and 97. The heat sinks are directly adjacent to the drive unit 99, by means of which the spindle 93 is driven to move the piston up and down. Furthermore, the filter unit 85 can be seen with which the inlet line 77 is fluidically coupled. In the illustration of FIG. 5, the filter frame 87, the replaceable filter unit 89 and the filter bowl 101 in which the replaceable filter 89 rests can also be seen. In this regard, the filter cover 87 is coupled to the filter bowl 101 by means of screws.

By means of the heat sinks, which may for example be made of milled metal, the heat generated in the actuator 99 can be better dissipated to the outside.

FIG. 6 shows further measures for dissipating heat from the drive unit. The hollow body 111 has a coating 113 of diamond-like carbon on its inner surface, which is characterized by particular smoothness and thus by reduced friction. The piston 115 has three grooves 117, 119, 121, circularly extending around the piston. A ring of Viton is disposed in each of the grooves 117 and 121, forming a seal between the outer wall of the piston and the inner wall of the hollow body 111. The groove 119 contains a reservoir for a cross-linked grease film, the purpose of which is to reduce friction between the O-ring 123 or 125 and the inner wall of the hollow body 111.

With reference to the sequence of FIGS. 7A-D, the suction process and the ejection process of the second chamber of the drive unit will be briefly discussed. FIGS. 7A-D each show only a section of the drive unit, and in particular only the piston, the second chamber and a schematic inlet and a schematic outlet.

Figure 7A:
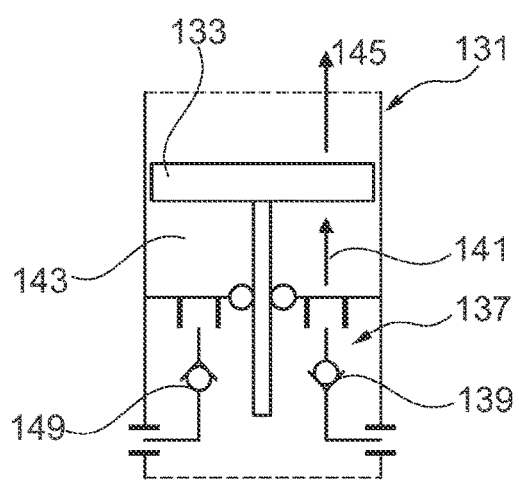

With respect to the drive unit 131, FIG. 7A shows that the piston 133 moves upward in the direction 135. This draws air 141 into the second chamber 143 through the inlet 137, which includes a check valve 139. As the stroke of the piston 133 increases, air 141 flows into the second chamber 143, providing good mixing and distribution of the drawn-in air throughout the chamber (see FIG. 7B).

Figure 7B:
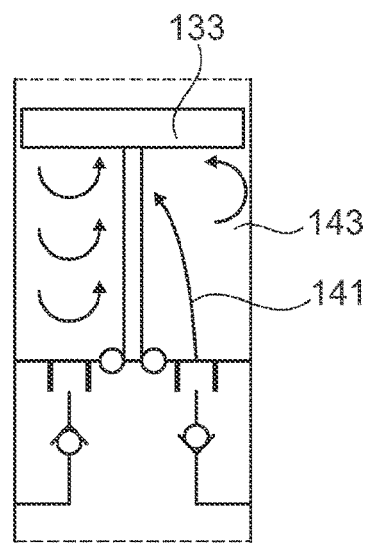
Figure 7C:
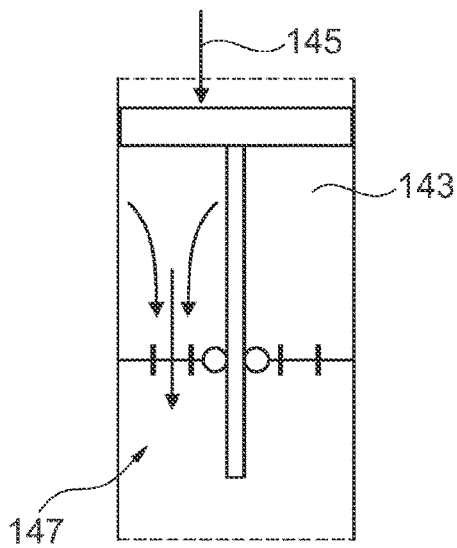
Figure 7D:
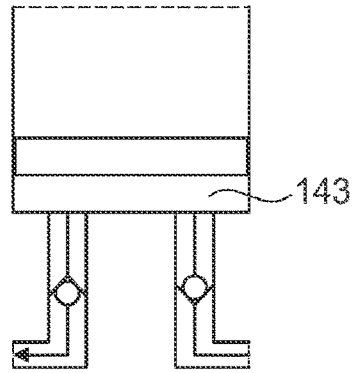

In FIG. 7B, the second chamber is at its maximum volume. In the subsequent lowering movement 145 as shown in FIG. 7C, the air present in the second chamber 143 can only escape through the outlet 147 and the check valve 149 located in the outlet. In this way, the heat absorbed by the air is supplied to the outside world and heat is transported out of the drive unit. When the second chamber reaches its minimum volume (see FIG. 7D), the cycle starts again and new cool and filtered air is drawn into the chamber through inlet 141.

Further embodiments will be apparent to the skilled person in an obvious manner.

To clarify the use of and to hereby provide notice to the public, the phrases "at least one of <A>, <B>, ... and <N>" or "at least one of <A>, <B>, ... <N>, or combinations thereof" or "<A>, <B>, ... and/or <N>" are defined by the Applicant in the broadest sense, superseding any other implied definitions hereinbefore or hereinafter unless expressly asserted by the Applicant to the contrary, to mean one or more elements selected from the group comprising A, B, ... and N. In other words, the phrases mean any combination of one or more of the elements A, B, ... or N including any one element alone or the one element in combination with one or more of the other elements which may also include, in combination, additional elements not listed. Unless otherwise indicated or the context suggests otherwise, as used herein, "a" or "an" means "at least one" or "one or more."

The application also covers the following aspects:
1. A drive unit (31) for a diaphragm pump (35), having a first hollow body (37) and a piston (39) which is arranged in the first hollow body such that it can move along an axis (z) of the hollow body, the piston dividing the hollow body into a first chamber (41) which can be connected to the diaphragm pump and a second chamber (43) which can be coupled to a gas reservoir, wherein the second chamber is coupled to an inlet valve (61) and an outlet valve (65) so that a gas flow is drawn into the chamber via the inlet valve and is forced out of the chamber via the outlet valve.
2. The drive unit according to aspect 1, wherein the inlet valve and/or the outlet valve is a check valve.
3. A drive unit according to any one of the previous aspects, wherein a filter unit (85) is provided, and the inlet valve preferably fluidically couples the filter unit and the second chamber.
4. The drive unit according to aspect 3, wherein the filter unit comprises a replaceable filter (89), and the filter is preferably held between a filter bowl (101) and a filter cover (87).
5. A drive unit according to any one of the preceding aspects, wherein at least one heat sink (95, 97) is provided, and the outlet valve fluidically couples the heat sink to the second chamber.
6. The drive unit according to any one of the preceding aspects, wherein an inlet (55) of the second chamber is coupled to the inlet valve (61) and an outlet (57) of the second chamber is coupled to the outlet valve (65).
7. The drive unit according to any one of the preceding aspects, wherein a motor (99) driving the piston is disposed below the second chamber.
8. The drive unit according to aspects 5 and 7, wherein the motor is thermally coupled to the at least one heat sink.
9. A drive unit according to any one of the preceding aspects, wherein a gap seal is disposed between an inner wall of the hollow body and the piston.
10. The drive unit according to aspect 9, wherein the gap seal comprises at least one O-ring (123, 125) preferably guided in at least one groove of the piston.
11. A drive unit according to any one of the preceding aspects, wherein the hollow body comprises a thermal coating (113).

The invention claimed is:

1. A drive unit for a diaphragm pump, the drive unit comprising:
   a first hollow body;
   a piston, wherein the piston divides the hollow body into a first chamber and a second chamber, the first chamber being configured to supply fluid to the diaphragm pump and the second chamber having an inlet valve and an outlet valve, wherein the second chamber is configured to draw a gas flow through the inlet valve and to force the gas flow out through the outlet valve to an outlet line;
   a motor driving the piston via a spindle extending through the second chamber from the motor to the piston, wherein the motor is disposed below the second chamber; and
   a heat sink comprising a monolithic first heat sink disposed below the second chamber and directly adjacent to the motor so as to be thermally coupled thereto, wherein the heat sink is thermally coupled to the motor and thermally and fluidically coupled to the second chamber via the outlet valve;
   wherein the outlet line is disposed within the first heat sink.

2. The drive unit of claim 1, wherein an inlet of the second chamber is coupled to the inlet valve and an outlet of the second chamber is coupled to the outlet valve.

3. The drive unit of claim 1, wherein the inlet valve and/or the outlet valve is a check valve.

4. The drive unit of claim 1, wherein a filter unit is provided, and the inlet valve-fluidically couples the filter unit and the second chamber.

5. The drive unit of claim 4, wherein the filter unit comprises a replaceable filter and the filter is held between a filter bowl and a filter cover.

6. The drive unit of claim 1, wherein a gap seal is arranged between an inner wall of the hollow body and the piston.

7. The drive unit of claim 6, wherein the gap seal comprises at least one O-ring guided in at least one groove of the piston.

8. The drive unit of claim 1, wherein the hollow body comprises a thermal coating.

* * * * *